(12) United States Patent
Limonadi

(10) Patent No.: US 9,254,216 B2
(45) Date of Patent: Feb. 9, 2016

(54) METHOD AND APPARATUS FOR LIMITING RANGE OF MOTION OF THE BODY OF THE USER

(76) Inventor: Farhad M. Limonadi, Rancho Mirage, CA (US)

( * ) Notice: Subject to any disclaimer, the term of this patent is extended or adjusted under 35 U.S.C. 154(b) by 0 days.

(21) Appl. No.: 13/557,113

(22) Filed: Jul. 24, 2012

(65) Prior Publication Data

US 2014/0026898 A1     Jan. 30, 2014

(51) Int. Cl.
    *A61F 5/01*            (2006.01)

(52) U.S. Cl.
    CPC ....................................... *A61F 5/013* (2013.01)

(58) Field of Classification Search
CPC .................................. A61F 5/013; A61F 5/01
USPC ............ 128/869, 878, 879, 882, 880; 602/20, 602/21, 32, 36; 482/44, 45, 46; 601/33, 40
See application file for complete search history.

(56) References Cited

U.S. PATENT DOCUMENTS

| | | | |
|---|---|---|---|
| 4,938,476 A | 7/1990 | Brunelle et al. |
| 5,042,505 A | 8/1991 | Mayer et al. |
| 5,469,861 A | 11/1995 | Piscopo et al. |
| 5,513,651 A | 5/1996 | Cusimano et al. |
| RE37,209 E | 6/2001 | Hensley et al. |
| 6,334,852 B1 | 1/2002 | Seyl |
| 6,402,708 B1 | 6/2002 | Sitte |
| 6,517,501 B1 | 2/2003 | Slautterback |
| 6,592,538 B1 | 7/2003 | Hotchkiss et al. |
| 6,723,061 B2 | 4/2004 | Williams |
| 6,834,436 B2 | 12/2004 | Townsend et al. |
| 6,852,067 B2 | 2/2005 | Limonadi |
| 7,210,240 B2 | 5/2007 | Townsend et al. |
| 7,698,830 B2 | 4/2010 | Townsend et al. |
| 7,850,574 B2 | 12/2010 | Narayanaswami |
| 8,025,632 B2 | 9/2011 | Einarsson |
| 2001/0020140 A1 | 9/2001 | Kramer |
| 2001/0031937 A1 | 10/2001 | Repice et al. |

(Continued)

FOREIGN PATENT DOCUMENTS

| KR | 10-2010-0089539 A | 8/2010 |
| KR | 20-2011-0002122 U | 3/2011 |

(Continued)

OTHER PUBLICATIONS

International Search Report and Written Opinion for PCT Application No. PCT/US2013/025415, mailed May 15, 2013, issued by the International Searching Authority (8 pages).

(Continued)

*Primary Examiner* — Victoria J Hicks
(74) *Attorney, Agent, or Firm* — Klarquist Sparkman, LLP

(57) ABSTRACT

An apparatus and method are disclosed for limiting the range of motion of a first portion of the body of a user relative to a second portion of the user's body. A body attachable device is secured to the first and second portion of the user's body. At least one elongated member extends between the first and second portions of the user's body for moving longitudinally as the user's body moves. A range of motion limiter restrains further longitudinal movement of the elongated member at the desired terminal end of the range of motion by receiving an adjustable stop secured to the elongated member. A stop adjustment enables the stop to be moved positionally to an adjusted position, whereby the terminal end of a range of motion can be adjusted by the user.

31 Claims, 12 Drawing Sheets

(56) References Cited

U.S. PATENT DOCUMENTS

2010/0249667 A1     9/2010    Narayanaswami
2011/0306471 A1    12/2011    Huang
2013/0072829 A1*    3/2013    Fausti et al. .................... 601/40

FOREIGN PATENT DOCUMENTS

| KR | 10-2011-0135165 A | 12/2011 |
|----|-------------------|---------|
| WO | WO/00/76400 | 12/2000 |
| WO | WO-01/37730 A1 | 5/2001 |
| WO | WO 01/49235 | 7/2001 |
| WO | WO/2005/055815 | 6/2005 |

OTHER PUBLICATIONS

International Search Report and Written Opinion issued by the Korean Intellectual Property Office on Sep. 5, 2013, for corresponding PCT Patent Application No. PCT/US2013/045364, 10 pp.

* cited by examiner

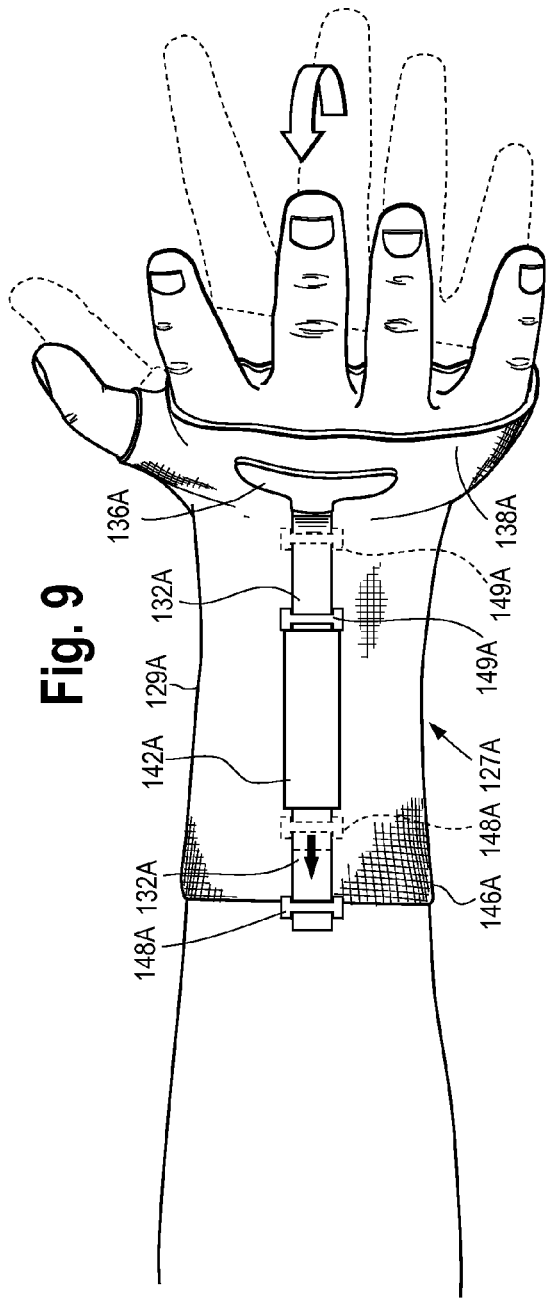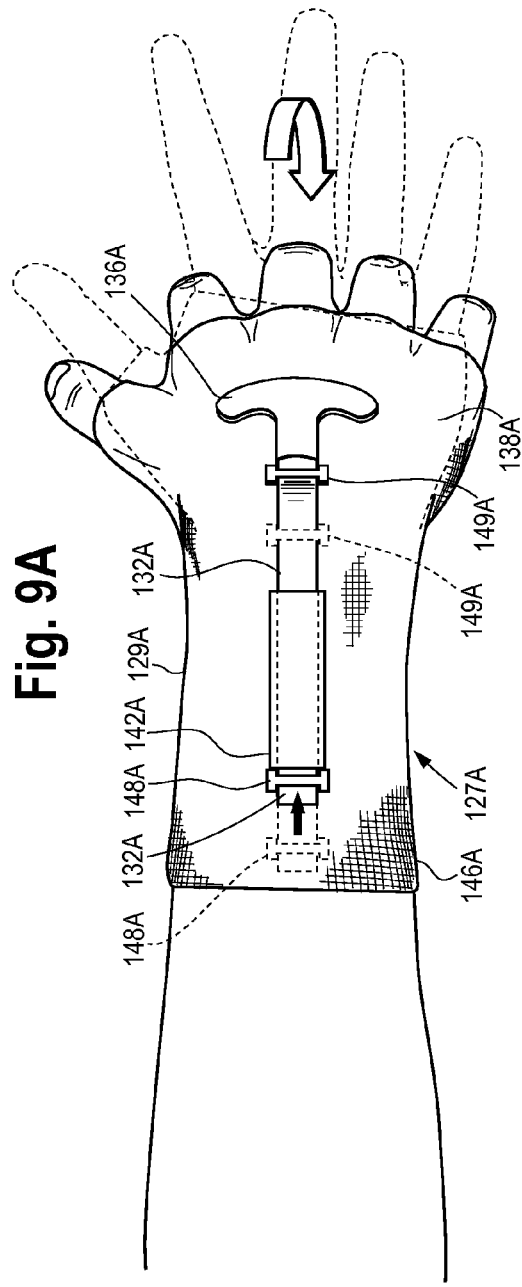

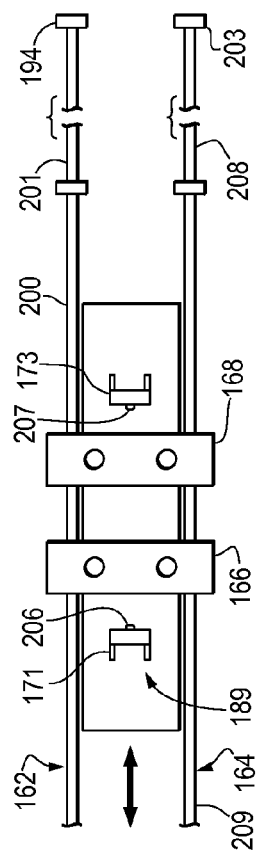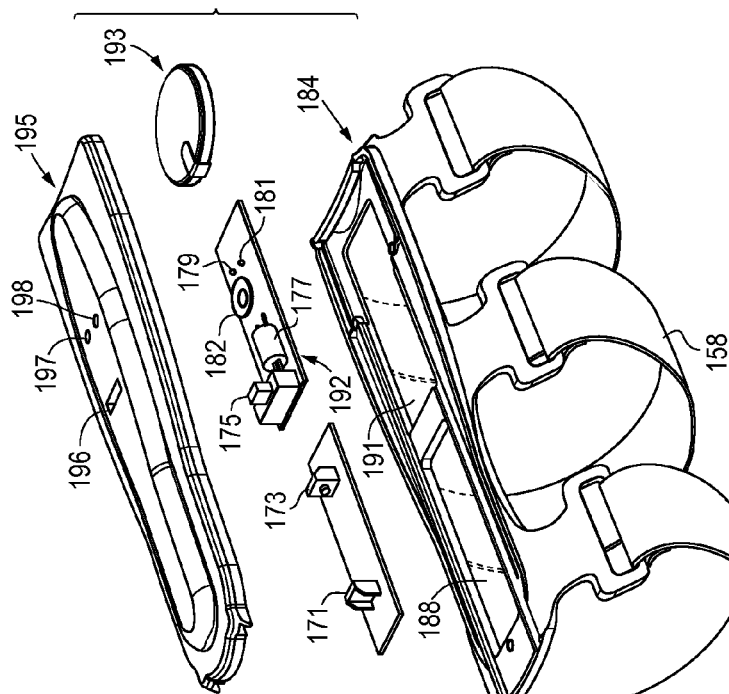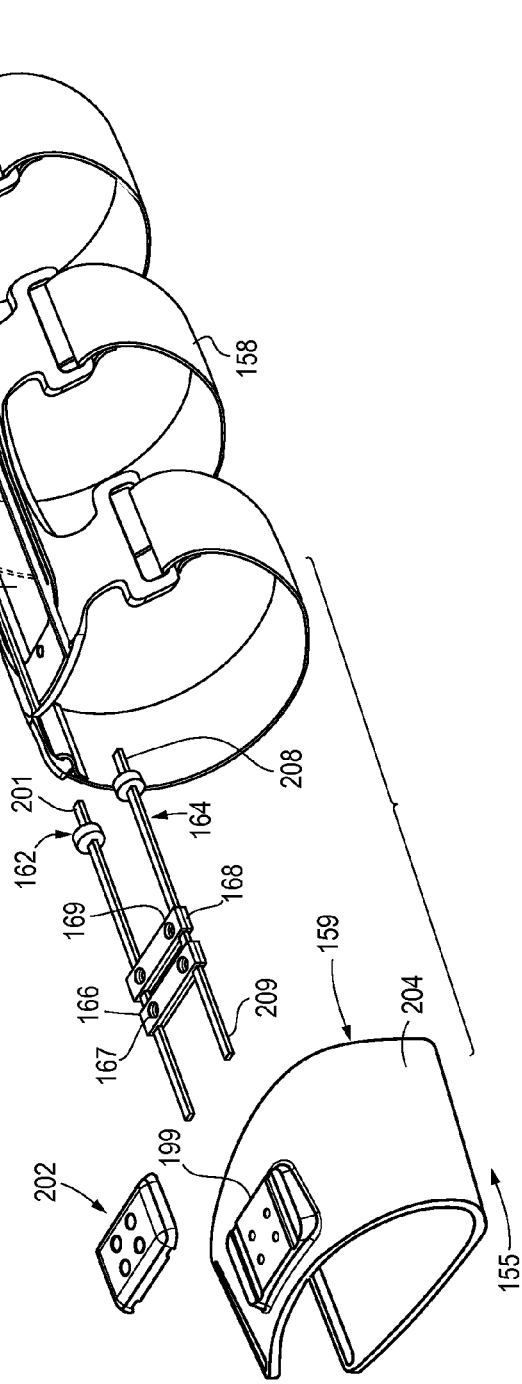

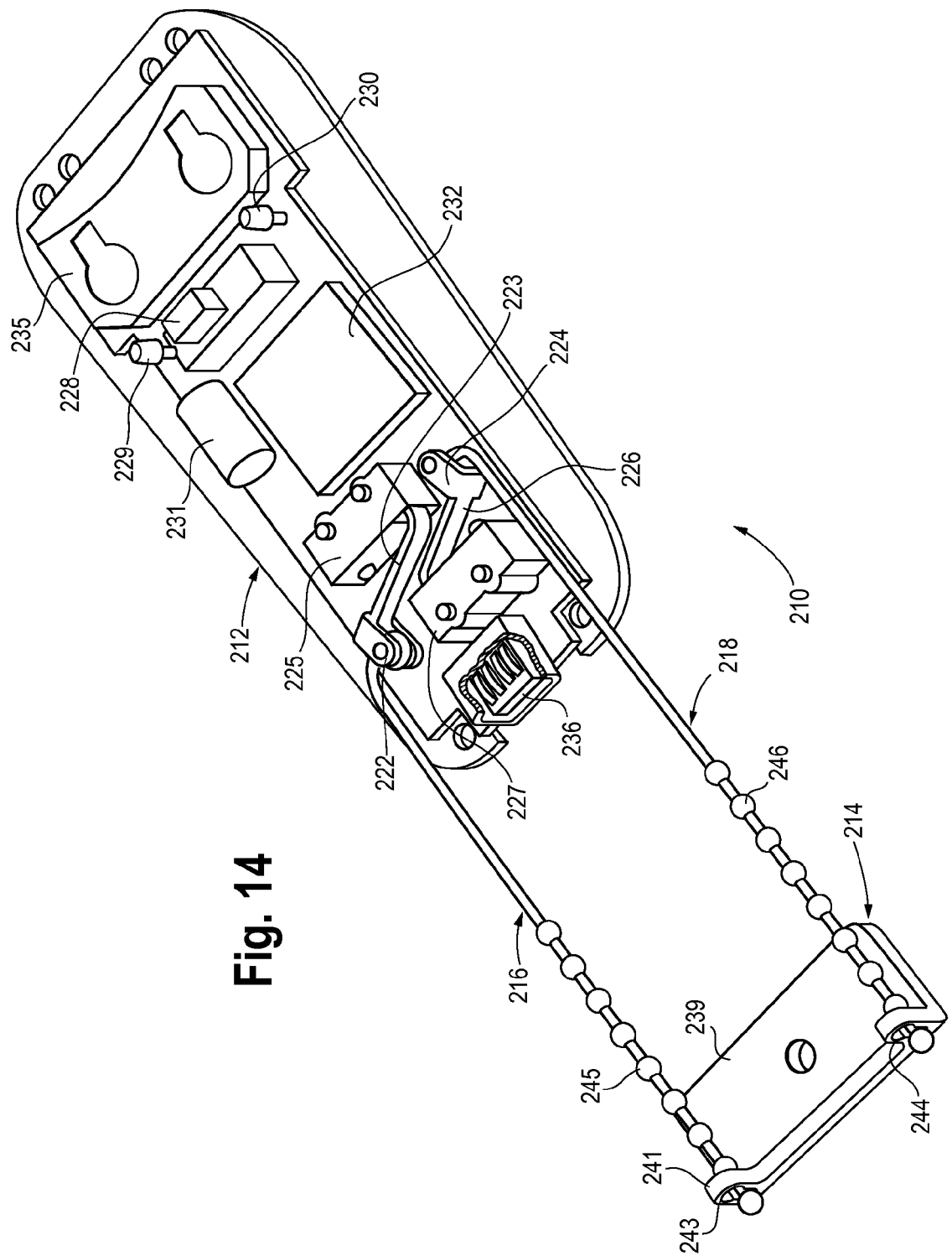

METHOD AND APPARATUS FOR LIMITING RANGE OF MOTION OF THE BODY OF THE USER

RELATED ART

This application incorporates by reference, as if fully set forth herein, U.S. provisional patent application No. 61/444,141, filed Feb. 18, 2011, entitled "METHOD AND APPARATUS/NOVEL SPLINT FOR TREATING CARPAL TUNNEL SYNDROME ANOTHER FOR BACK PAIN."

FIELD

The present disclosure relates to a method and apparatus for limiting the range of motion of a person's body. It more particularly relates to such a method and apparatus for limiting the range of motion of a first portion of the user's body relative to a second portion of the user's body such as the various joints and back of a person's body to prevent or to treat maladies.

BACKGROUND ART

This section describes the background art of the disclosed embodiment of the present invention. There is no intention, either express or implied, that the background art discussed in this section legally constitutes prior art.

Various different devices and methods have been used to facilitate the prevention and treatment of various maladies such as carpal tunnel syndrome which is a nerve disorder in the hands. In the case of carpal tunnel syndrome, wrist splints have been used to fix the wrist in either a neutral or extended position. However, such devices have proven to be less than successful in permanently controlling or relieving symptoms in at least some applications.

For record purposes, the following is a list of US and foreign patents relating to various other attempts to prevent or treat maladies of the body caused by one portion of the body moving relative to another portion of the body such as at various joints or movement of the person's back: U.S. Pat. Nos. 4,938,476; 5,042,505; 5,513,651; 6,402,708; 6,852,067; WO/00/076400; and WO/05/055815.

In U.S. Pat. No. 6,852,067, issued to the same inventor as the inventor of the present application, there is disclosed devices used for facilitating the prevention and treatment of maladies such as carpal tunnel syndrome. The devices permit limited range of motion to allow the patient to perform normal use of the hands and yet alert the patient to stop further movements when the hands are nearing an unsafe hyperextended or flexed position. Also, one of the patented devices may provide a mechanically selectively lockable pivot joint to limit mechanically the allowable extension and flexion of a hand piece relative to a forearm piece of a splint. Inner and outer cylinders are mounted at the wrist for receiving locking pins which limit the rotation of the inner cylinder relative to the other cylinder.

While such a device is quite acceptable for some applications, it would be desirable to accomplish the adjustable limits to the user's range of motion without attaching a device to the side of the wrist of the user. In this regard, it would be highly desirable to have a device which is more compact and less bulky, and therefore less restrictive to the user during normal use of the hands.

BRIEF DESCRIPTION OF THE DRAWINGS

In order to better understand the invention and to see how the same may be carried out in practice, non-limiting preferred embodiments of the invention will now be described with reference to the accompanying drawings, in which:

FIGS. 9 and 9A are plan views of yet another apparatus similar to the apparatus of FIG. 6 constructed according to yet another embodiment;

FIG. 11 is an exploded view of the apparatus of FIG. 10;

FIG. 12 is an enlarged detailed plan view of the limit switch assembly of the apparatus of FIG. 10;

FIG. 14 is an exploded view with a portion thereof broken away for illustration purposes, of the apparatus of FIG. 12.

DETAILED DESCRIPTION OF CERTAIN EMBODIMENTS

Figure 1:
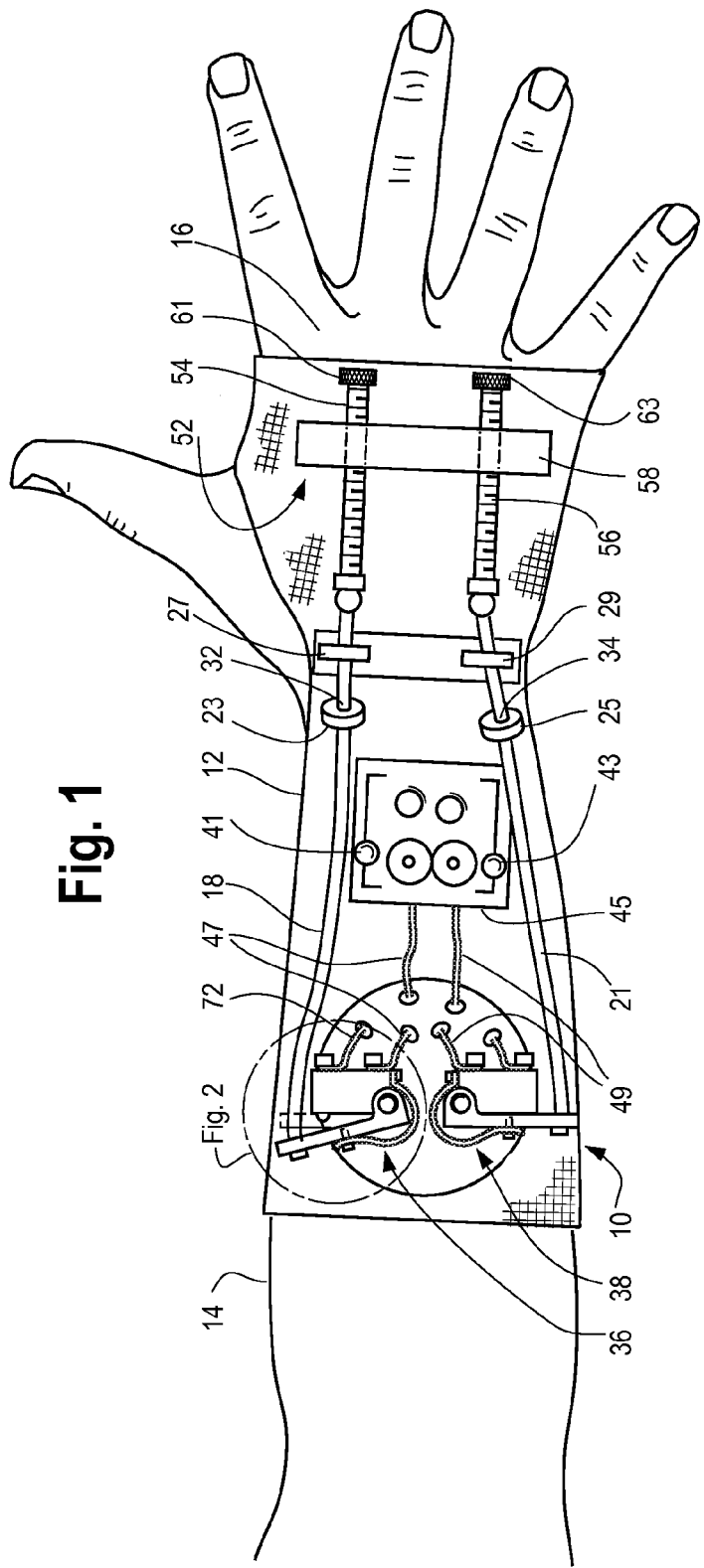
FIG. 1 is a plan view of an apparatus which is constructed in accordance with an embodiment, and which is shown worn on the forearm and hand of the user.

Certain embodiments of the present invention will now be described more fully hereinafter with reference to the accompanying drawings, in which some, but not all, embodiments of the invention are shown. Indeed, these embodiments of the invention may be in many different forms and thus the invention should not be construed as limited to the embodiments set forth herein; rather, these embodiments are provided as illustrative examples only so that this disclosure will satisfy applicable legal requirements. Like numbers refer to like elements throughout.

It will be readily understood that the components of the embodiments as generally described and illustrated in the drawings herein, could be arranged and designed in a wide variety of different configurations. Thus, the following more detailed description of the certain ones of the embodiments of the system, components and method of the present invention, as represented in the drawings, is not intended to limit the scope of the invention, as claimed, but is merely representative of the embodiment of the invention.

An apparatus and method are disclosed for limiting the range of motion of a first portion of the body of a user relative to a second portion of the user's body. A body attachable device is secured to the first and second portion of the user's body. At least one elongated member extends between the first and second portions of the user's body for moving longitudinally as the user's body moves. A range of motion limiter restrains further longitudinal movement of the elongated member at the desired terminal end of the range of motion by receiving an adjustable stop secured to the elongated member. Stop adjustment means enables the stop to be moved positionally to an adjusted position, whereby the terminal end of a range of motion can be adjusted by the user.

According to other embodiments, there is provided a method which limits the range of motion of a first portion of the body relative to a second portion of the body. The method includes attaching at least one elongated member to the first and second portion of the user's body for moving longitudinally as the user's body moves. Further longitudinal movement of the elongated member is restrained or stopped at the terminal end of a desired range of motion of the first portion of the user's body. Further longitudinal movement of the elongated member is prevented or restrained by engaging an adjustable stop with a limiter at the desired terminal end of the range of motion.

Figure 2:
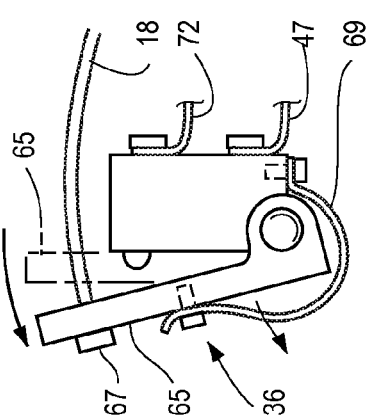
FIG. 2 is an enlarged view of one of the limit switches of the apparatus of FIG. 1.

Referring now to the drawings more particularly to FIGS. 1 and 2 thereof, there is disclosed an apparatus 10, which limits adjustably the range of motion of a first portion of the body of a user relative to a second portion of the user's body, and which is constructed in accordance with one embodiment. The apparatus 10 is adapted to be worn on the forearm and hand of the user preferably to prevent and treat carpal tunnel syndrome. The apparatus 10 is compact in construction to enable the user a greater degree of freedom of the use of his or her hand, and yet prevents flexing of the hand to an extent which would be unsafe for the user. The apparatus can also provide warning signals to the user when the hand is flexing toward an unsafe position. It should be understood that the apparatus 10 may also be employed effectively for other joints or the user's back to prevent or treat maladies.

The apparatus 10 includes a body attachable means or device in the form of an elastic sleeve 12 secured to the first body part (the forearm 14) of the user and secured to the second body part (the hand 16) of the user. A pair of elongated members in the form of cords 18 and 21 are mounted on the dorsal side of the sleeve 12 and extend between the forearm 14 and the hand 16. The cords 18 and 21 may be resilient and move longitudinally as the body of the user moves. A resilient cord may be composed of any suitable stretchable material. It is to be understood that there may be employed other types and kinds of cords, such, for example, as non-stretchable cords having attached thereto springs, elastic material or others. By employing the cords and their associated components on the dorsal side of the sleeve 12, forearms and hands can rest normally on tables, desks or the like during normal use of the hands.

A pair of adjustable stops in the form of apertured discs 23 and 25 are attached to the respective cords 18 and 21 by being threaded frictionally thereon. They can be conveniently slid along their respective cords to positionally adjust the stops to stop the hand 16 from flexing beyond a certain desired range of motion. A pair of range of motion limiters in the form of eyelets 27 and 29 are mounted on the sleeve 12 in a fixed manner to prevent the stops 23 and 25 from further movement as the hand 16 flexes relative to the forearm 14. Stop adjustment means in the form of holes 32 and 34 in the respective discs 23 and 25 receive the respective cords 18 and 21 in a friction tight manner, so that when the discs 23 and 25 are pulled into engagement with the eyelets 27 and 29 as the hand flexes, further movement of the cords are prevented and the hand 16 is restrained or inhibited from further flexing.

In order to warn or alert the user that his or her flexing of the wrist is approaching an unsafe position, either during extension or flexion, a normally open limit switch 36 and a normally closed limit switch 38 activate warning devices such as the LEDs 41 and 43 to provide for visual alerts for the user. It should be understood that other types of warning signals or alerts may be employed such as audible or tactile alerts in a similar manner. Also, it should be understood that different warning signals such as different colors or flashing frequencies of the LED, different tones of the audible devices and/or different frequencies of the tactile devices, may be generated. One type of warning signal may correspond to excessive flexion of the wrist, and a different output signal may correspond to excessive extension of the wrist. Furthermore, the warning signal may become progressively more prominent as the flexing wrist approaches the unsafe position. In this regard, the frequency of the flashing LED or the tactile device may progressively increase, or the tones of the audible device may increase progressively in volume or frequency.

A circuit board 45 mounted on the sleeve 12 controls the LEDs 41 and 43 or other warning devices (not shown) by means of the limit switches 36 and 38 which are electrically connected to the printed circuit board 45. Conductor leads 47 connect the limit switch 36 to the printed circuit board 45, and similarly the conductor leads 49 connect the limit switch 38 to the circuit board 45.

While a general form of a limit switch is shown in the drawings in the form of a spring activated switch for explanation purposes, it should be understood that different types and kinds of limit switches such, for example, as microswitches, magnet switches, optical switches, and others, may be used. As used herein, the terms "normally open" means that the contacts of the switch are not electrically connected and therefore the circuit is in a certain state. The terms "normally closed" refer to the contacts being electrically connected to activate the circuit to cause it to be in a certain state. In the embodiment of FIG. 1, the limit switch 36 is normally open with its contacts spaced apart in an unstressed condition in its OFF state. The limit switch 38 is normally closed with its contacts connected in a stressed or biased position also in its OFF state. When the limit switches 36 and 38 are closed or opened respectively, they each enter its ON state to activate its respective LED 41 or 43.

The cord 18 is normally in a slack condition when the hand is in its neutral position as shown in FIG. 1. When the hand 16 flexes, it pulls the normally open limit switch 36 into its closed position to illuminate the LED 41. Alternatively, both of the LEDs 41 and 43 may be illuminated for attention attracting purposes.

The cord 21 is normally in a tensioned condition during the normal mode of operation when the hand 16 is in its neutral position as shown in FIG. 1, and the limit switch 38 is releasably disposed in its normally closed position. When the hand 16 moves toward or into a hyper-extended position, the cord 21 relaxes and permits the limit switch 38 to spring into its open position, which in turn causes the LED 43 to illuminate. Alternatively, when the limit switch 38 moves into its open position, both LEDs 41 and 43 may be illuminated.

It should be understood that as used herein, the term "slack condition" in referring to the cords 18 and 21, both cords could be under some tension. However, the tension in the cord 18 is under normal condition below the threshold required to actuate the limit switch 36 and hence activate the circuit for its LED 41 when the wrist is hyper flexed. The tension on the cord 21 on the other hand under normal condition is above the threshold required to actuate the circuit for its LED 43, and therefore the lever is in its closed position and its LED is not activated in normal use. When the wrist is hyper-extended, the cord tension goes below this threshold, the lever of the actuator is released and the alarm LED 43 is activated.

When the hand 16 flexes, both of the discs 23 and 25 are pulled by the respective cords 18 and 21 into engagement with the thick eyelets 27 and 29 to restrain the hand from further moving in a flexed position. Thus, when the hand is flexing, and is moving toward an unsafe position, the LED 41 may first be illuminated to warn the user to stop moving in that direction. However, if the user continues to move in a flexing direction, the discs 23 and 25 will engage the eyelets 27 and 29 to provide a hard stop for further movement by the user. To adjust the position where the discs engage the eyelets, the discs may be slid manually along the cords to adjusted positions.

A warning signal adjustment generally indicated at 52 enables the user to conveniently adjust the tension on the cords 18 and 21 so that the limit switches 36 and 38 can be activated sooner or later for both flexing and hyper-extending movements of the hand 16. The adjustment 52 includes a pair of threaded rods 54 and 56 journaled for rotation in a bar 58 fixed to the hand portion of the sleeve 12 and connected to ends of the cords 18, 21, respectively. A pair of thumb knobs 61 and 63 on the front ends of the respective threaded rods 54 and 56 enable the user to manually rotate selectively either one or both of the threaded rods 54 and 56. Longitudinal movement of a rod 54, 56 is effective to adjust the tension on the corresponding cord 18, 21.

Considering now the limit switches in greater detail with particular reference to FIG. 2, the two limit switches are similar to one another, except that the flexion limit switch 36 is normally permitted to remain in its open position as shown in FIG. 1 due to the slack condition of the cord 18. The hyper-extension limit switch 38 is normally pulled into its closed position by the tension cord 21 as shown in FIG. 1. Only the limit switch 36 will now be described in greater detail with reference to FIG. 2. The limit switch 36 includes a pivotally movable contact arm 65 which is attached at its distal end to the cord 18 by an enlarged end 67. A leaf spring 69 biases the contact arm in a switch open position. When the hand 16 moves into a flexed position, the cord 18 pulls the contact arm 65 into its closed position for switching the electrical power from the lead 72 to the lead 47 for illuminating the LED 41.

Figure 3:
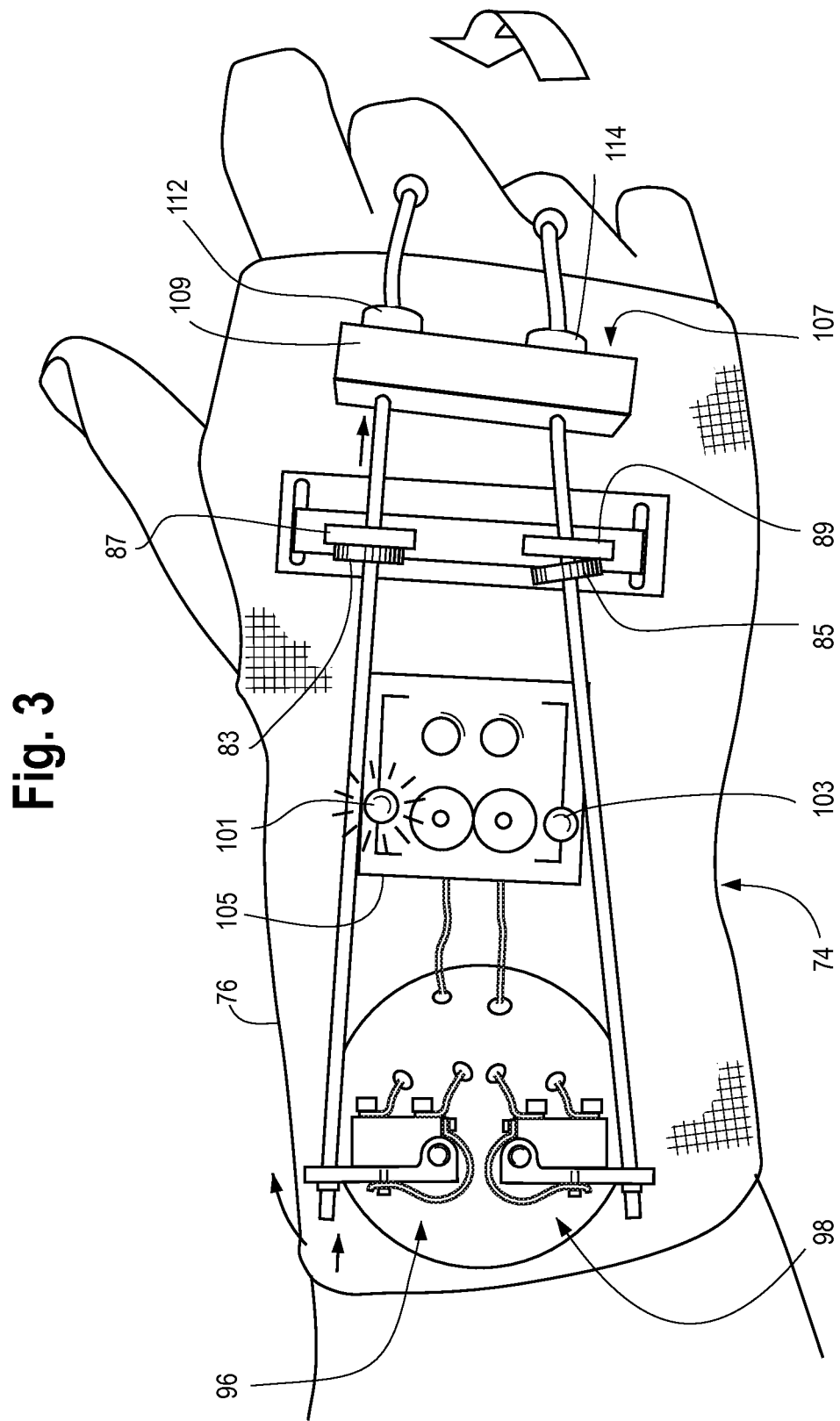
FIG. 3 is a plan view of another apparatus which is constructed in accordance with another embodiment, and which is illustrated showing the hand moved toward a flexed position.
Figure 4:
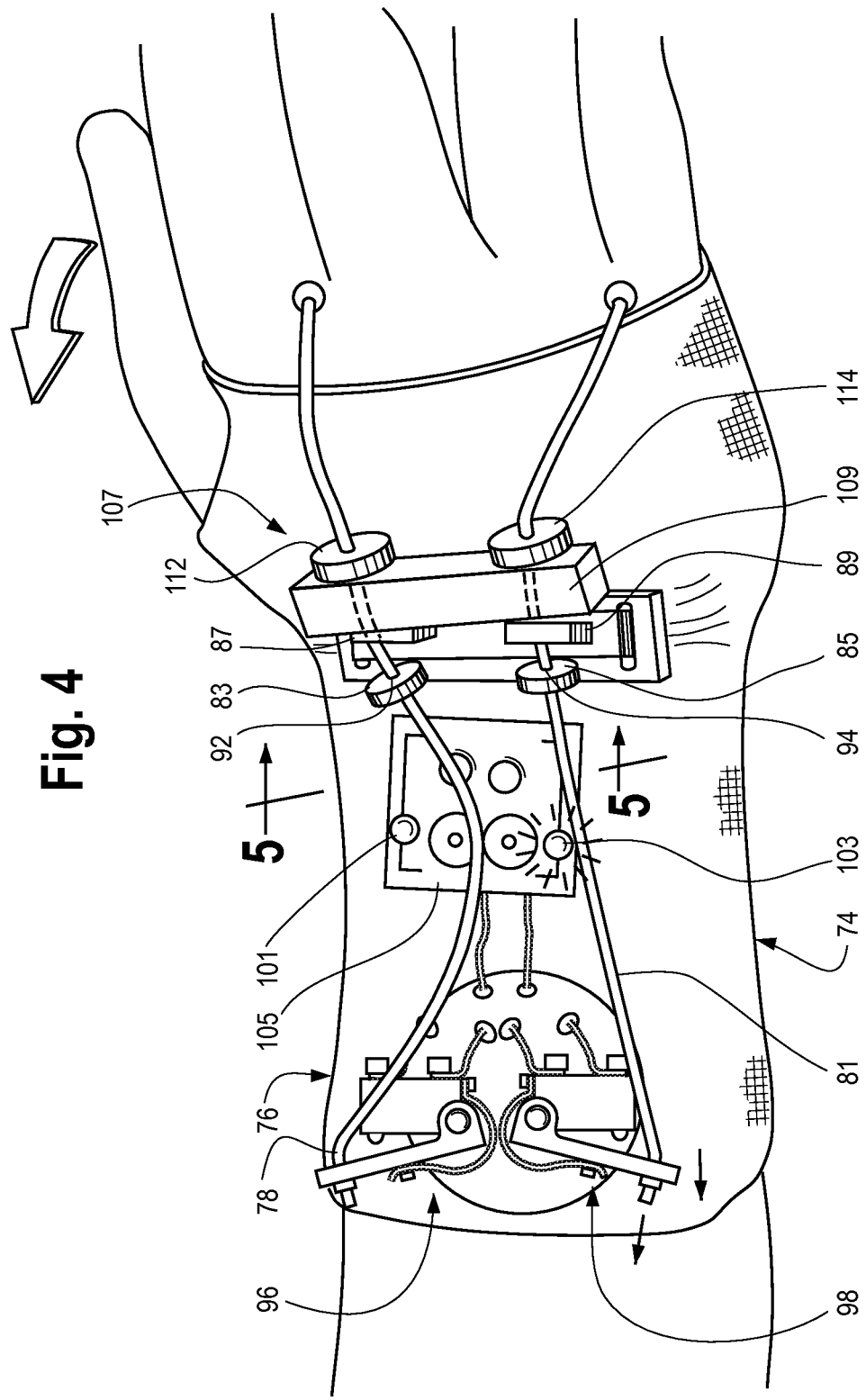
FIG. 4 is a plan view of the apparatus of FIG. 3, illustrating it with the hand moved toward a hyper-extended position.
Figure 5:
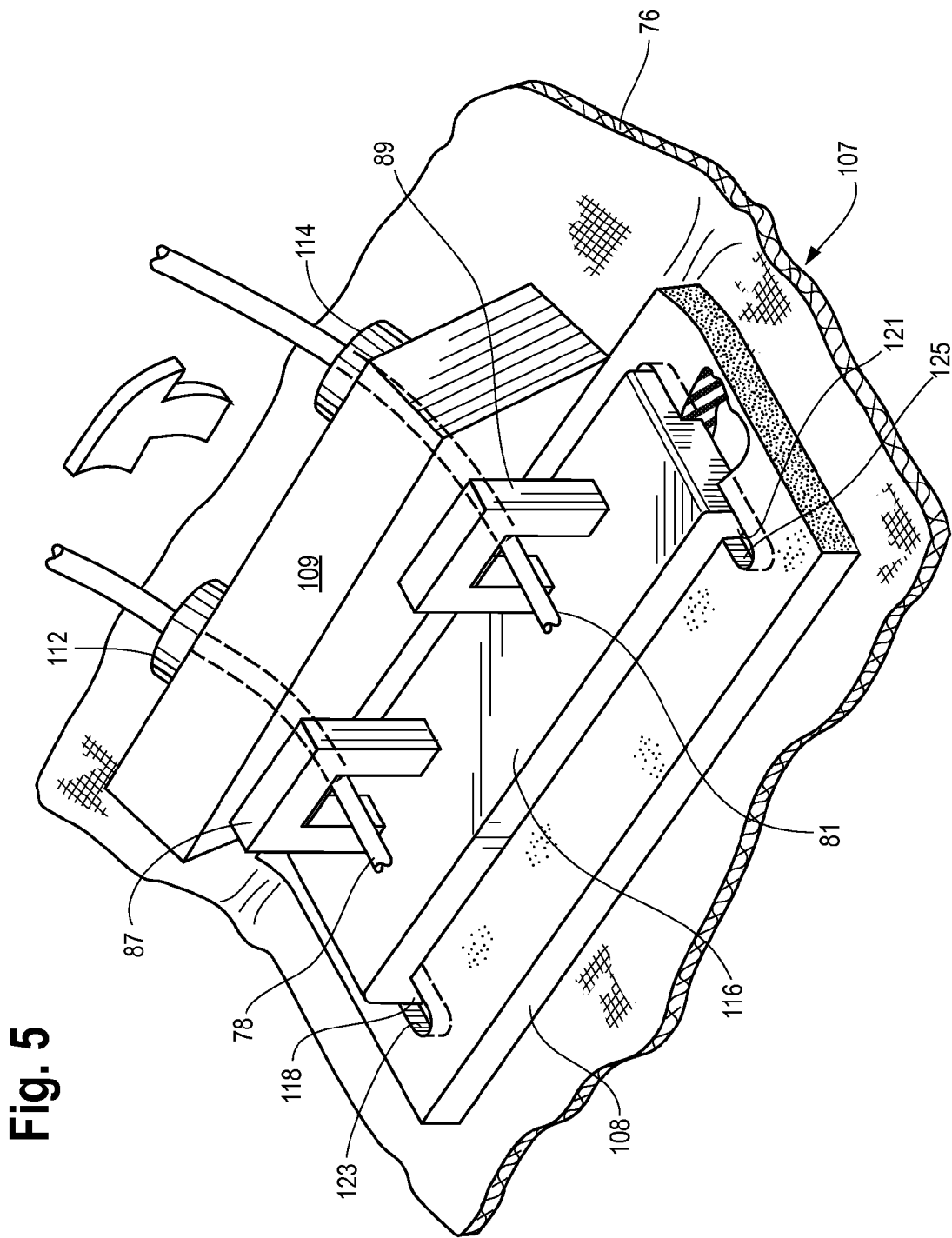
FIG. 5 is an enlarged fragmentary partially broken away view of the warning signal adjustment of the apparatus of FIG. 4.

Referring now to FIGS. 3, 4 and 5 of the drawings, there is shown another embodiment of a range of motion limiting apparatus 74, which is constructed in accordance with another embodiment, and which is similar to the apparatus 10, except that it has an alternate version of the warning signal adjustment and it provides for a hard stop in both the flexing and hyper-extending movements of the hand of the user. The apparatus 74 generally comprises a body attachable means in the form of a sleeve 76 which is similar to the sleeve 12 of FIG. 1. The apparatus 74 also includes a pair of elongated members in the form of resilient cords 78 and 81 which are similar to the cords of the apparatus 10. Additionally, a pair of adjustable stops in the form of discs 83 and 85 are similar to and perform the same function as the discs 23 and 25 of the apparatus 10.

A pair of adjustable range of motion limiters in the form of movable eyelets 87 and 89 cooperate with the adjustable stop discs 83 and 85 in a similar manner as the eyelets 87 and 89 cooperate with the discs 83 and 85 of FIG. 1. However, the eyelets 87 and 89 are also positionally adjustable and serve to limit or restrain the extent of the hyper-extending of the hand as hereinafter described in greater detail. The discs 83 and 85 have stop adjustment means in the form of holes 92 and 94 for receiving the respective cords 78 and 81 for the same purpose as the holes 32 and 34 for the discs 23 and 25 of FIG. 1. Limit switches 96 and 98 serve similar purposes as the respective limit switches 36 and 38 of the apparatus 10. In this regard, the limit switches 96 and 98 activate warning devices in the form of LEDs 101 and 103 to provide alerts to the user when the hand of the user is moving toward the end of a desired range of motion either in a flexing or hyper-extending movement of the hand. A circuit board 105 is similar to the board 45. As shown in FIG. 3, when the hand flexes to the end of its safe range of motion, the LED 101 is illuminated and the discs 83 and 85 engage the eyelets 87 and 89, respectively, to prevent or restrain further flexing movement of the hand of the user. Alternatively, when the hand moves into a hyper-extended position as shown in FIGS. 4 and 5 of the drawings, the LED 103 is illuminated and further hyper-extending movement of the hand is restrained or prevented as hereinafter described in greater detail.

As shown in FIG. 5, a warning signal adjustment 107 includes a base plate 108 fixed on its underside to the sleeve 76 in a similar manner as the bar 58 of FIG. 1 and has the front end portions of the cords 78 and 81 threaded through apertures in a bar 109 so that tensioners in the form of apertured discs 112 and 114 frictionally receiving the cords 78 and 81 respectively. In this manner, the user can adjustably tension the cords by adjusting the position of the cords relative to the apertured bar 109 threaded onto and carried by the cords 78 and 81, by simply holding the ends of the cords and sliding the discs along the cords into adjusted positions, so that the tension on the cords 78 and 81 can be adjusted whereby the LED lights will be illuminated either earlier or later as desired.

The bar 109 serves as a stop when the wrist is moved toward a hyper-extended position (FIGS. 4 and 5), by engaging the eyelets 87 and 89. In order to adjust the stopping position during the hyper-extending movement of the hand, the upstanding eyelets 87 and 89, as best seen in FIG. 5, are positionally adjustable relative to the sleeve 76. A carriage strip 116 supports from below the U-shaped eyelets 87 and 89 in upright positions on top thereof, and includes a pair of downwardly depending flanges 118 and 121 at the opposite ends thereof for fitting frictionally and slideably within a pair of longitudinally extending elongated adjustment slots 123 and 125, respectively. In this manner, the flanges 118 and 121 frictionally engage the slots 123 and 125, respectively, and are movable manually in a longitudinal direction toward and away from the bar 109. In this manner, the bar 109 will engage the eyelet 87 and 89 either sooner or later, depending upon the position of the eyelets 87 and 89 relative to the position of the bar 109.

Referring now to FIGS. 6, 7, 8 and 9 of the drawings, there is shown a range of motion limiting apparatus 127, which is constructed in accordance with yet another embodiment. The apparatus 127 is similar to the apparatus 10, except that it has range of motion limiting devices on both the dorsal and the palmer sides of the apparatus and does not employ the electronics for providing early warning or alerts. However, it should be understood that the other embodiments of warning components disclosed herein, including the electronics described above, may be employed with the apparatus 127. The apparatus 127 is a simplified, compact apparatus which allows for a limited range of motion of the hand of the user, and yet restrains or prevents movement in either the flexing or hyper-extending motions of the hand.

The apparatus 127 includes a body attachable means in the form of an elastic sleeve 129 which is similar to the sleeve 12 of FIG. 1. An elongated member in the form of a flexible deformable strip 132 preferably composed of metal material and is disposed and extends along the dorsal side of the sleeve 129. A similar elongated member in the form of a flexible deformable strip 134 is disposed and extends along the palmer side of the sleeve 129. The elongated members are used to prevent the movement of the hand beyond a desired adjustable range of motion of the hand.

Figure 6:
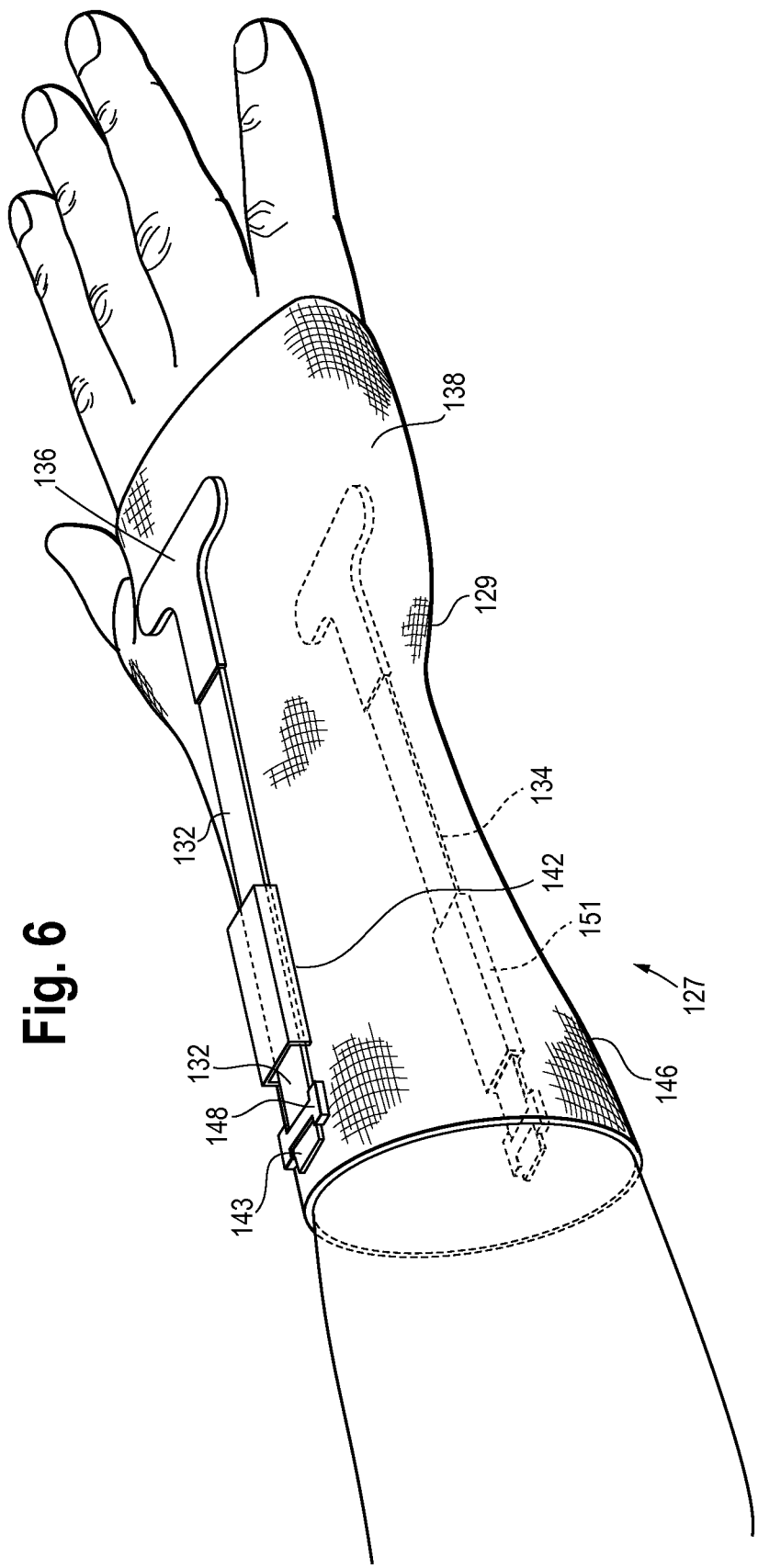
FIG. 6 is a pictorial view of a further apparatus which is constructed in accordance with a further embodiment, and which is illustrated with the hand in a neutral position.
Figure 7:
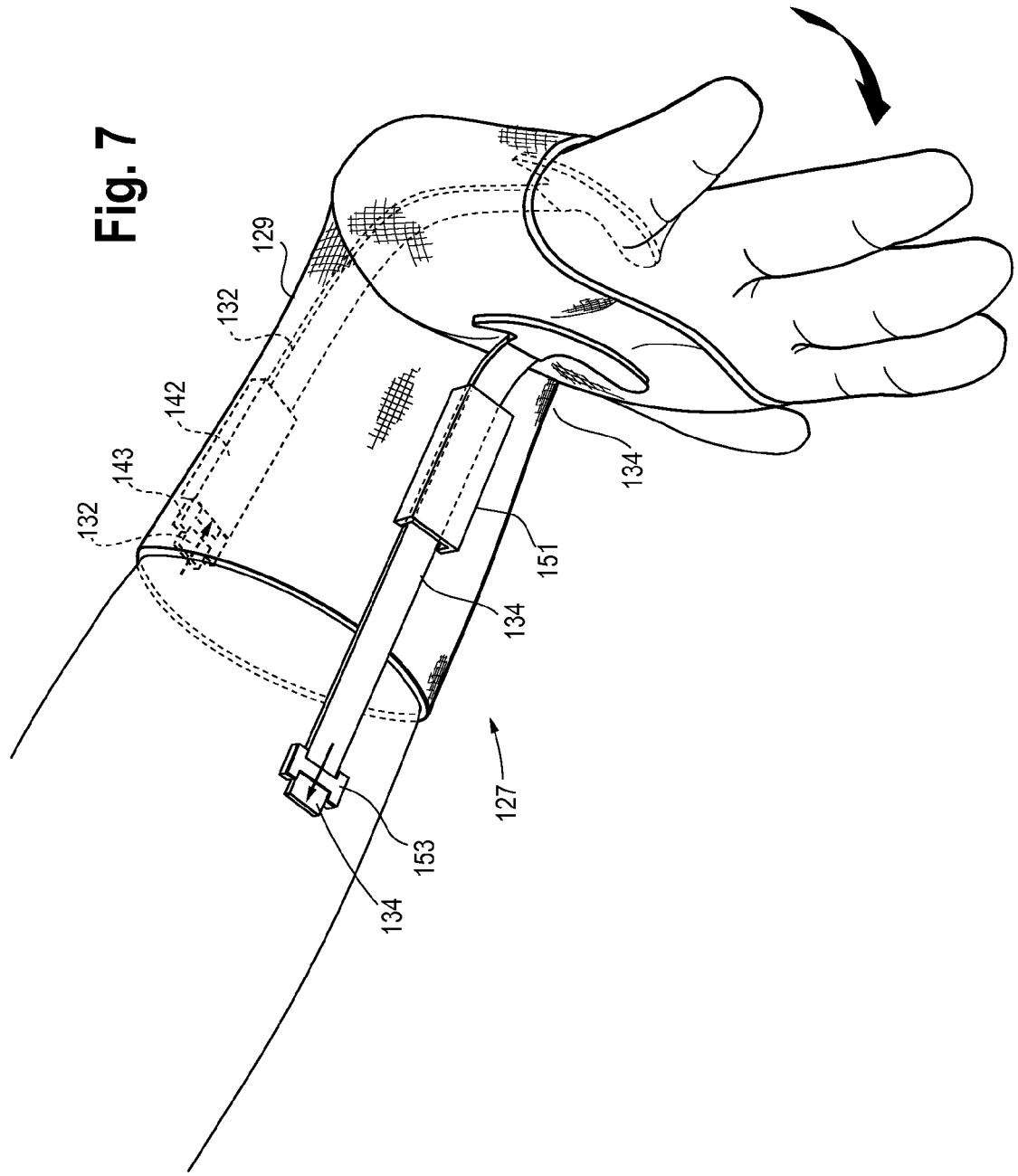
FIG. 7 is a pictorial view of the apparatus of FIG. 6, illustrating the hand moved toward a flexed position.
Figure 8:
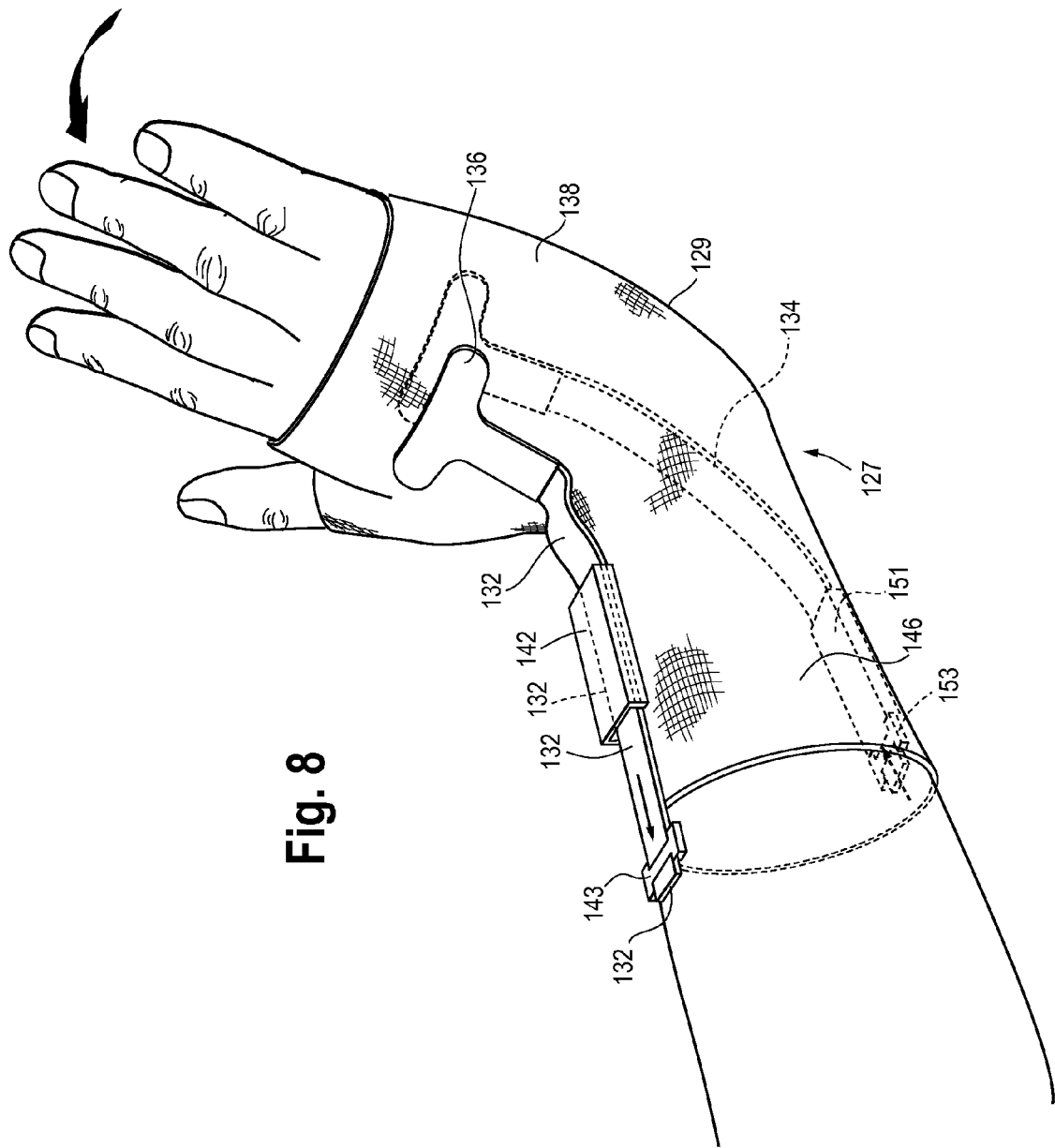
FIG. 8 is a pictorial view of yet another apparatus of FIG. 6, illustrating the hand moved toward a hyper-extended position.

Considering now, the device on the dorsal side of the sleeve 129 with particular reference to FIGS. 6, 7 and 8, a T-shaped connector 136 fixes a front end of the metal strip 132 to the hand or forward end portion 138 of the sleeve 129. A range of motion limiter fixed to the sleeve 129 in the form of a flattened tubular contact 142 serves as a guide for the metal strip 132 to enable it to slide back and forth freely along the forearm portion of the sleeve 129 at the rear end of the strip 132 for receiving and engaging an adjustable stop 148 slideably mounted on the rear end of the strip 132 at a forearm portion 146 of the sleeve 129. When the hand moves from a neutral position shown in FIG. 6 toward a flexed position as shown in FIG. 7, the stop 148 engages the end of the fixed tubular contact 142, thereby preventing or restraining further flexing of the wrist. The adjustable stop 148 is frictionally engaged to the strip 132, and is able to be moved manually by the user into a positionally adjusted manner for adjusting suitably the range of motion permitted in a flexed manner. It should be noted that when the stop 143 is pulled into engagement with the contact 143 (FIG. 7), the palmer strip 134 is free to move backwardly through the contact 151.

Considering now the strip 134 on the palmer side of the sleeve 129, a range of motion limiter in the form of a flattened tubular contact 151 is similar to the flattened contact 142 and freely receives the strip 134 to enable it to slide freely back and forth through the contact 151. An adjustable stop 153 is similar to the adjustable stop 148 and functions in a similar manner to limit the slideable movement of the strip 134 when the hand moves toward a hyper-extended position as shown in FIG. 8. The stop 153 is carried by the strip 134 forwardly until it engages the fixed contact 151 to prevent or revisit further movement of the wrist toward a hyper-extended position. In so doing, the dorsal strip 132 moves forwardly freely through the contact 142.

It should be noted that the metal strips 132 and 134 are pliable and flexible. It should be understood that these strips may be composed of any other suitable material, such as plastic material, composite material, or other. Also, the strip may have any suitable cross sectional shape, such, for example, as circular, rectangular, triangular or other. Also, the strip may be in the form of a rod or other.

Referring to FIGS. 9 and 9A, there is shown a range of motion limiting apparatus 127A, which is constructed according to another embodiment and is similar to apparatus 127, except that two adjustable stops 148A and 149A may alternatively engage the ends of a limiter in the form of a flat tubular contact such as the flat tubular contact 142A.

The parts of the apparatus 127A, which correspond to the parts of the apparatus 127, have the same reference characters with the addition of a letter A as the reference characters for the apparatus 127. The strops are fixed to a strip 132A at a forearm portion such as the portion 146A of the sleeve 129A to enable adjustable limiting of the extent of flexion and extension of the wrist using only a single dorsal or palmar metal strip and associated components. The stops 148A and 149A are positioned on the strip 132A at opposite ends of the contact 142A, whereby the contact 149A engages the front-end of the contact 142A when the hand moves toward a hyper-extended position (FIG. 9). Similarly, the stop 148A engages the rear end of the elongated contact 142A when the wrist flexes as shown in FIG. 9A.

Figure 10:
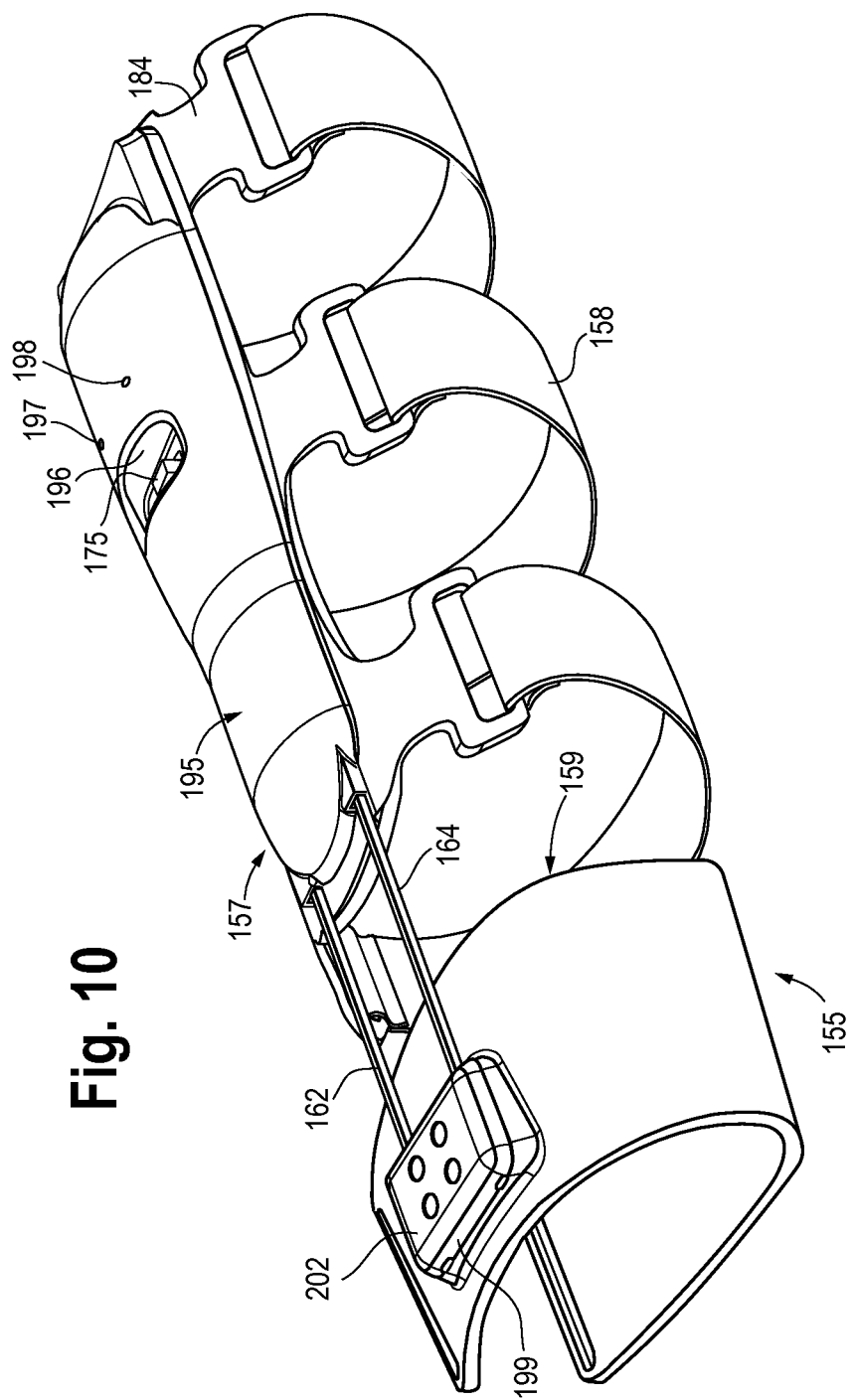
FIG. 10 is a pictorial view of yet another apparatus which is constructed in accordance with yet another embodiment.

Referring now to FIGS. 10 and 11, there is shown a range of motion limiting apparatus 155, which is constructed in accordance with a further embodiment, and which does not employ an elastic sleeve as the foregoing disclosed embodiments of the present invention. Instead, the apparatus 155 has a body attachable means including a forearm attachable means or device 157 which is attachable to the forearm of the user by means of Velcro straps, such as a Velcro strap 158. The forearm attachable means or device 157 may also be other types and kinds of securing devices, such as other stretchable members such as bands. The body attachable means of the apparatus 155 also includes a hand attachable device or means in the form of a band 159. A pair of elongated members in the form of flexible rods or wires 162 and 164 interconnect the forearm attachable device 157 and the hand attachable device 159, whereby flexible rods or wires 162 and 164 slide into and out of the forearm attachable device 157 as the hand of the user moves into a hyper-extended position or a flexed position. The flexible rods 162 and 164 may be composed of any suitable material such, for example, as metal, plastic, composite or other materials or combinations thereof. Also, it should be understood that while a pair of parallel extending rods is currently preferred, a single rod may instead be employed and may be wider than the illustrated rods 162 and 164 such as a flat strip or other. The apparatus 155 prevents or firmly resists the hand from moving toward or beyond the end of a desired range of motion in either the flexed or the hyper-extended positions of the hand. Furthermore, alerts may be provided to warn the user that the hand is approaching the end of a desired range of motion.

As shown in FIG. 11, an adjustable stop 166 is positionally adjustably fixed across the pair of parallel disposed elongated members or wires 162 and 164. The stop 166 is a clamp formed of a pair of clamping plates which are secured together by a pair of screws such as the screw 167. The clamp 166 is adjustably positioned along the wires 162 and 164 to prevent or to restrain further flexion movement of the hand as hereinafter described in greater detail.

An adjustable stop 168 is formed of a pair of plates secured by screws such as the screw 169 across the wires 162 and 164 to the rear of the stop 166 for preventing or limiting further movement of the hand in a hyper-extended motion as hereinafter described in greater detail.

An adjustable range of motion limiter in the form of a stationary limit switch 171 fixed in place on the forearm attachable device 157 is adapted to be engaged by the stop 166 when the hand moves in a flexed position. Similarly, the adjustable range of motion limiter may also include a limit switch 173 spaced from the limiter 171 for receiving the stop 168 to prevent or restrain further motion of the hand in an excessively hyper-extended movement.

The limit switches 171 and 173 each provide an electrical signal to cause alerts to be generated by warning devices before the user's hand moves in an excessive extension or flexion manner. In this regard, a three-position switch 175 is manually movable by the user to select a predetermined first position where a pair of warning devices in the form of LEDs 179 and 181 provide a visual alert signal to the user. In a second position, both a warning device in the form of a vibrator 177 providing a tactile signal and the pair of LEDs 179 and 181 are activated so that both a tactile and a visual alert is given to the user. In a third position of the switch 175, a warning device in the form of a speaker 182 is activated to provide an audible alert signal to the user, together with the signals from the vibrator 177 and the LEDs 179 and 181. It is to be understood that other combinations of alerts may also be employed by the three position switch 175, such as having three separate signals comprising only the tactile vibration signal in the first position, only the visual signal in the second position, and only the audible signal in the third position.

Considering now the apparatus 155 in greater detail, the forearm detachable device 157 includes a forearm housing 184, which may be formed of suitable material such as thermoplastic material. The housing 184 includes a printed circuit board pocket 188 for receiving a limit switchboard 189 which supports the limit switches 171 and 173. A printed circuit board pocket 191 receives the three-position switchboard 192, which supports the three-position switch 175, as well as the vibrator 177, LEDs 179 and 181, and the speaker 182, as well as a rechargeable battery 193.

A cover 195 is secured to the forearm housing 184 and includes a three-position switch opening 196 to enable the user to gain access to the switch 196. A pair of holes 197 and 198 to expose the light from the LEDs 179 and 181.

The band 159 includes a pair of clamp plates 199 and 202 for fixing the front ends of the pair of wires 162 and 164 to a removable hand strap 204.

Referring now to FIGS. 11 and 12, the wires 162 and 164 may be provided with stretchable portions. The wire 162 includes a stretchable resilient portion 200 composed of suitable slightly resilient material such as rubber or other elastomeric material, and a flexible non-stretchable portion 201 which may be composed of a suitable flexible material such as metal, plastic or other. Similarly, the wire 164 includes a stretchable resilient portion 209 and a flexible non-stretchable portion 208. As shown in FIG. 12, a pair of anchors 194 and 203 fixedly secure the ends of the respective stretchable portions 201 and 208 to the forearm housing 184. A pair of longitudinally extending grooves such as the groove 205 receive the wires 162 and 164. The adjustable stops 166 and 168 extend between and are releasably fixed to the wires 162 and 164 in a position between the limit switches 171 and 173. When the hand of the user flexes, the wires 162 and 164 are pulled forwardly until the stop 166 engages a switch button 206 on the flexion limit switch 171 to activate the devices such as the LEDs 179 and 181. It should be noted that the flexion limit switch 171 may mechanically limit further movement of the hand in a flexing motion, although the hand can move to a greater extent depending upon the resiliency of the wires 162 and 164.

Similarly, when the hand of the user moves toward a hyper-extended position, the wires 162 and 164 slide backwardly to enable the adjustable stop 168 to move into engagement with a switch button 207 on the limit switch 173 to activate warning devices such as the LEDs 179 and 181. In this manner, the limit switch 173 may serve to mechanically resist the further hyper-extending motion of the wrist. By adjusting the position of the adjustable stops 166 and 168 toward or away from their respective limit switches 171 and 173, the warning or alert devices such as the LEDs 179 and 181 may be activated sooner or later depending upon the adjusted position of the stops. As a result, the stops may be moved positionally to an adjusted position, whereby the terminal end of a range of motion of the stop may be adjusted by the user.

Figure 13:
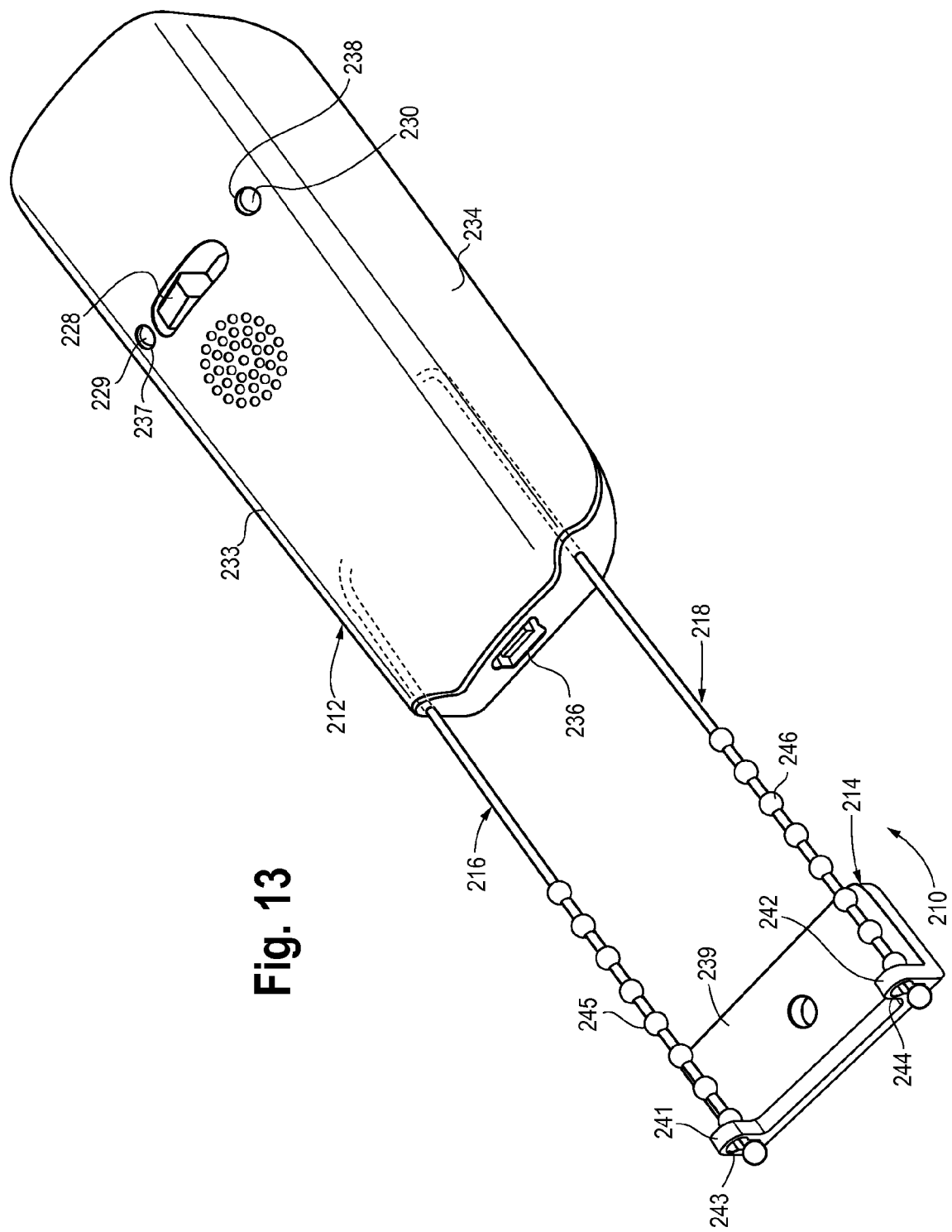
FIG. 13 is a pictorial view of a still further apparatus which is constructed in accordance with a still further embodiment.

Referring now to FIGS. 13 and 14, there is shown a range of motion limiting apparatus 210, which is also constructed in accordance with a further embodiment of the present invention, and which is similar to the apparatus 155 except for the arrangement of the parts to activate the limit switches in an adjustable manner. The apparatus 210 has a body attachable means which includes a forearm attachable means or device 212 which is similar to the device 157 and may be attached to the forearm of the user by any suitable means such as Velcro, straps, an elastic sleeve or other. In this regard, the apparatus 155 may also be mounted on a conventional brace adapted to extend between the forearm and the hand of the user. The body attachable means of the apparatus 210 further includes a hand attachable device or means 214, which is similar to the device 159. A pair of parallel spaced-apart stretchable elongated members such as cords, rods or wires 216 and 218 interconnect the forearm attachable device 212 and the hand attachable device 214. The wires 216 and 218 may be at least partially composed of a resilient material such as rubber or other elastomeric materials. Being stretchable, the wires 216 and 218 permit the wrist of the user to move toward a hyper-extended position or a flexed position.

As shown in FIG. 14, an adjustable stop 222 fixed to an end of the wire 216 and also fixed to an end of a blade or lever 223 of a stationary or adjustably movable limit switch 225. In this manner, the limit switch 225 activates an alert when the hand of the user moves the hand attachable device 214 toward a hyper-extended position so that the wire 216 pushes the blade 223 into engagement with the limit switch 225 to cause an alert for the user. In the embodiment where the wire is composed of a resilient material such as rubber or other elastomeric material, the wire undergoes a compressive force to cause it to slide backwardly within a groove (not shown) within the forearm device 212 against the force of the spring biased blade 223, which is thus forced to close the limit switch 225.

Similarly, a blade or lever 226 of a stationary or adjustably movable limit switch 227 is fixed to an adjustable stop 224, which in turn is connected to the rear end of the wire 218. In this manner, when the hand of the user flexes at the wrist to move the hand attachable device 214 away from the forearm attachable device 212 in a manner to pull the wire 218 forwardly, which in turn causes the stop 224 to move the blade 226 into engagement with the limit switch 227 for causing an alert to be generated for the user. The stretchable wires 216 and 218 enable the wrist to move into either a hyper-extended position or a flexed position. Once the blades 223, 226 move into engagement with their respective limit switch, the further flexing or extending movements of the hand are thereafter restricted only by the further stretchability of the wires 216 and 218.

The apparatus 210 further includes a 3-position switch 228 which is similar to the 3-position switch 196, controlling warning devices in the form of a pair of LEDs 229 and 230, as well as a vibrator 231 and a speaker 232 positioned near speaker openings 223 (FIG. 13) in the forearm housing 234. A rechargeable battery housing 235 containing a battery (not shown) activates circuit components (not shown) for activating the alert devices. A USB port 236 enables the battery in the battery housing 235 to receive a USB cable (not shown) for charging the battery for the apparatus 210, and also for conveying information to a computer (not shown) for recording information from the use of the apparatus 210. A pair of holes 237 and 238 in the forearm housing 234 enabled the LEDs 229 and 230 to be seen by the user during the use of the apparatus 210.

Considering now the hand attachable device 214 in greater detail, the device 214 has a stop adjustment including a plate 239 having a pair of upstanding flanges 241 and 242 which includes respective keyhole openings 243 and 244 for receiving enlargements or beads such as the beads 245 and 246 of the respective wires 216 and 218. In this regard, each one of the wires 216 and 218 include a series of enlargements or beads which can be slipped through their respective keyhole openings and then engage the openings adjustably in such a manner as to trap their respective wire in an adjusted position. Due to the stretchable characteristic of the wires 216 and 218, the user can pull on the wires to stretch them and extend them through their respective keyhole openings until a desired tension is applied to the wires. Each keyhole opening has a first portion larger in diameter than the beads (that allows the beads to pass through the flange when adjusting the corresponding wire) and a second, narrower portion that has a width smaller than the diameter of the beads (that prevents the beads from passing through the flange once the desired tension of the wire is achieved). In adjusting the tension of the wires, the stops 222 and 224 move adjustably the blades 223 and 226, respectively, farther away from or closer to their respective limit switches 225 and 227 from the positions as indicated in FIG. 14, to adjust the range of motion through which the blades 223, 226 travel to activate their respective switches 225, 227. The alerts from the warning devices are thereby activated adjustably to adjust the range of motion of the user by warning him or her that further movement in such a direction could be harmful. In this regard, by pulling on either one of the wires 216 and 218 from the position illustrated in FIG. 14 into an adjusted position, the corresponding blade 223 or 226 is caused to flex accordingly. The blade 223 is flexed somewhat to assume a position further away from its switch 225 so that the wire 216 must move when the wrist extends toward a hyper-extended position, thereby enabling the user to extend the wrist further before the physical stop 222 prevents further movement and the alert is sounded. Similarly, the wire 218, when moved to an adjusted position from the position shown in FIG. 14, pulls the blade 226 to flex it and thus cause it to assume a position somewhat closer to its switch 227 to shorten the range of motion when a flexing movement of the wrist is undertaken.

Although the invention has been described with reference to the above examples, it will be understood that many modifications and variations are contemplated within the true spirit and scope of the embodiments of the invention as disclosed herein. Many modifications and other embodiments of the invention set forth herein will come to mind to one skilled in the art to which the invention pertains having the benefit of the teachings presented in the foregoing descriptions and the associated drawings. Therefore, it is to be understood that the invention shall not be limited to the specific embodiments disclosed and that modifications and other embodiments are intended and contemplated to be included within the scope of the appended claims. Although specific terms are employed herein, they are used in a generic and descriptive sense only and not for purposes of limitation.

The invention claimed is:

1. An apparatus for limiting a range of motion of a first portion of a user's body relative to a second portion of the user's body, comprising:
a body attachable device for securing to the first and second portions of the user's body;
at least one elongated member mounted on the body attachable device extending between the first and second portions of the user's body for moving longitudinally as the user's body moves;
a range of motion limiter mounted on the body attachable device for stopping further longitudinal movement of the at least one elongated member at a terminal end of a selected range of motion of the first portion of the user's body; and
a stop mounted on the at least one elongated member and being movable therewith upon movement of the user's body, the stop being configured to engage the range of motion limiter to prevent further longitudinal movements of the at least one elongated member at the terminal end of the selected range of motion; and
the stop being adjustable along the length of the at least one elongated member so as to adjust the terminal end of the selected range of motion.

2. An apparatus according to claim 1, further including warning signal devices activated by movement of the at least one elongated member.

3. An apparatus according to claim 2, wherein the at least one elongated member is a first elongated member, the body attachable device further including a pair of limit switches and a second elongated member, wherein the warning signal devices are activated by the pair of limit switches being controlled by the respective first and second elongated members, one of the first or second elongated members being in tension normally and one of the first or second elongated members being in a slack condition normally.

4. An apparatus according to claim 3, further including a warning signal adjustment including a bar.

5. An apparatus according to claim 4, wherein the bar also serves as a stop during hyper-extension of the user's hand for moving into engagement with the range of motion limiter.

6. An apparatus according to claim 5, wherein the range of motion limiter includes at least one eyelet for receiving the at least one elongated member, a carriage strip for supporting from below the at least one eyelet and having at least one flange slideably and frictionally secured within an elongated adjustment slot to enable adjustment of the selected terminal end of the range of motion.

7. An apparatus according to claim 4, wherein the warning signal adjustment includes a pair of threaded rods journalled for rotation in the bar.

8. An apparatus according to claim 4, wherein the warning signal adjustment includes a pair of discs, with a respective disc being frictionally threaded onto each of the first and second elongated members for engaging the bar.

9. An apparatus according to claim 2, wherein the at least one elongated member is a first elongated member, the body attachable device further including a pair of limit switches and a second elongated member, wherein the warning signal devices are activated by the pair of limit switches being controlled by respective of the first or second elongated members, whereby one limit switch of the pair of limit switches activates warning signal devices when a wrist is hyper-extended and the other limit switch of the pair of limit switches activates warning signal devices when the wrist flexes.

10. An apparatus according to claim 9, wherein the first and second elongated members are each stretchable resiliently and each has a series of spaced apart enlarged portions adapted to be engaged adjustably in flanges having openings therein.

11. An apparatus according to claim 1, wherein the at least one elongated member is a first elongated member, and further including a second elongated member mounted on the body attachable device extending between the first and second portions of the user's body for moving longitudinally as the user's body moves.

12. An apparatus according to claim 11, wherein the first and second elongated members extend substantially parallel to one another on a dorsal side of the body attachable device.

13. An apparatus according to claim 11, wherein the first elongated member is disposed on a dorsal side of the body attachable device, and the second elongated member is disposed on a palmer side of the body attachable device.

14. An apparatus according to claim 1, wherein the stop includes a clamp releasably fixed to the at least one elongated member.

15. An apparatus according to claim 14, wherein the clamp includes at least one fastening device to release the clamp to adjust positionally the clamp along the at least one elongated member.

16. An apparatus according to claim 1, wherein the body attachable device is an elastic sleeve.

17. An apparatus according to claim 1, wherein the body attachable device includes a forearm attachable part and a separate hand attachable part, the at least one elongated member interconnecting the forearm attachable part and the hand attachable part.

18. An apparatus according to claim 1, where the at least one elongated member is comprised of a material selected from the group consisting of metal, plastic, composition material, elastic material.

19. An apparatus according to claim 1, wherein the range of motion limiter includes an eyelet.

20. An apparatus according to claim 1, wherein the range of motion limiter includes a flattened tubular sleeve.

21. An apparatus according to claim 1, wherein the body attachable device includes a limit switch.

22. An apparatus according to claim 1, wherein the stop is a disc threaded onto the at least one elongated member.

23. An apparatus according to claim 1, wherein the at least one elongated member is a flexible rod, and the stop is slideably mounted on the flexible rod.

24. An apparatus for limiting a range of motion of a first portion of a user's body relative to a second portion of the user's body, comprising:
  a body attachable device for securing to the first and second portions of the user's body;
  at least one elongated member mounted on the body attachable device extending between the first and second portions of the user's body for moving longitudinally as the user's body moves;
  a range of motion limiter mounted on the body attachable device for stopping further longitudinal movement of the at least one elongated member at a terminal end of a selected range of motion of the first portion of the user's body; and
  a stop mounted on the at least one elongated member and being movable therewith upon movement of the user's body, the stop being configured to engage the range of motion limiter to prevent further longitudinal movements of the at least one elongated member at the terminal end of the selected range of motion, the stop being adjustable along the length of the at least one elongated member so as to adjust the terminal end of the selected range of motion; and
  a warning signal device configured to be activated by movement of the at least one elongated member.

25. An apparatus according to claim 24, wherein the at least one elongated member is a first elongated member, and further including a second elongated member mounted on the body attachable device extending between the first and second portions of the user's body for moving longitudinally as the user's body moves.

26. An apparatus according to claim 25, wherein the first and second elongated members extend substantially parallel to one another on a dorsal side of the body attachable device.

27. An apparatus according to claim 25, wherein the first elongated member is disposed on a dorsal side of the body attachable device, and the second elongated member is disposed on a palmer side of the body attachable device.

28. An apparatus according to claim 24, wherein the body attachable device includes a forearm attachable part and a separate hand attachable part, the at least one elongated member interconnecting the forearm attachable part and the separate hand attachable part.

29. A method for limiting a range of motion of a first portion of a user's body relative to a second portion of the user's body, comprising:
  attaching at least one elongated member to the first and second portions of the user's body for moving longitudinally as the user's body moves;
  restraining further longitudinal movement of the at least one elongated member at a terminal end of a selected range of motion of the first portion of the user's body by engaging a range of motion limiter with a stop mounted on the at least one elongated member, the stop being movable with the elongated member upon movement of the user's body;
  wherein the stop is adjustable along the length of the at least one elongated member so as to adjust the terminal end of the selected range of motion.

30. A method according to claim 29, further including generating warning signals in response to movement of the at least one elongated member.

31. A method according to claim 29, further including engaging the range of motion limiter with the stop for avoiding both excessive extension or flexion of the first portion of the user's body relative to the second portion of the user's body.

* * * * *